US007999122B2

(12) United States Patent
Langer et al.

(10) Patent No.: US 7,999,122 B2
(45) Date of Patent: Aug. 16, 2011

(54) METHOD OF PURIFYING VINYLENE CARBONATE

(75) Inventors: Reinhard Langer, Tönisvorst (DE); Paul Wagner, Düsseldorf (DE); Heinrich Grzinia, Erkelenz (DE)

(73) Assignee: SALTIGO GmbH, Langenfeld (DE)

( * ) Notice: Subject to any disclaimer, the term of this patent is extended or adjusted under 35 U.S.C. 154(b) by 604 days.

(21) Appl. No.: 11/920,169

(22) PCT Filed: May 4, 2006

(86) PCT No.: PCT/EP2006/004156
§ 371 (c)(1),
(2), (4) Date: Nov. 9, 2007

(87) PCT Pub. No.: WO2006/119910
PCT Pub. Date: Nov. 16, 2006

(65) Prior Publication Data
US 2009/0023936 A1  Jan. 22, 2009

(30) Foreign Application Priority Data
May 12, 2005  (DE) .................. 10 2005 021 966

(51) Int. Cl.
*C07D 317/36* (2006.01)
(52) U.S. Cl. ...................................... 549/230
(58) Field of Classification Search .................. 549/230
See application file for complete search history.

(56) References Cited

U.S. PATENT DOCUMENTS

| 2,873,230 A | 2/1959 | Thomas |
| 6,395,908 B1 | 5/2002 | Seifert |
| 2009/0234141 A1* | 9/2009 | Langer et al. ............... 549/230 |

FOREIGN PATENT DOCUMENTS

| GB | 957003 | 4/1964 |
| JP | 2000 026449 A | 1/2000 |
| JP | 2002 322171 A | 11/2002 |

OTHER PUBLICATIONS

Newman M.S. and Addor R.W. 1953. Vinylene Carbonate. JACS. vol. 75: 1263-1264.
Johnson W.K. and Patton T.L., 1960. Preparation of Vinylene Carbonate. JOC vol. 25: 1042.
Huang J., et al. 1990. Investigations on Vinylene Carbonate I. Preparation and Properties of Poly-(Vinylene Carbonate). Chinese J. Polymer Science, 8(3): 197-203.
Newman M.S. and Addor R.W. 1953. Synthesis and Reactions of Vinylene Carbonate. JACS vol. 77: 3789-3793.
Ding L., Li Y., Jiang Y., Cao Z., Huang J.. 2002. New Supports for Enzyme Immobilization based on Copolymers of Vinylene Carbonate and β-Hydroxyethylene Acrylate. J. of Applied Polymer Science, vol. 83: 94-102.
Ding L., Li Y., Li Yue, Liang Y., Huang J. 2001. Polymerization of vinylene carbonate as well as aminolysis and hydrolysis of poly(vinylene carbonate). European Polymer J., vol. 37: 2453-2459.

* cited by examiner

*Primary Examiner* — Bernard Dentz
(74) *Attorney, Agent, or Firm* — Michael A. Miller

(57) ABSTRACT

The present invention relates to the industrial purification of vinylene carbonate (VC).
It was found that it is advantageous to subject the VC to be purified, before the purifying distillation, to a simple thermal treatment with organic compounds which have amidic nitrogen-hydrogen bonds.

4 Claims, No Drawings

METHOD OF PURIFYING VINYLENE CARBONATE

The present invention relates to the industrial purification of vinylene carbonate (VC).

Vinylene carbonate is an important intermediate for the production of chemicals, pharmaceutical products, crop protection agents and in particular for polymers, coatings and battery electrolytes.

Vinylene carbonate is produced by a known method by eliminating hydrogen chloride from chloroethylene glycol carbonate (CGC) by means of tertiary amines, in particular triethylamine.

Chloroethylene glycol carbonate is obtained by free radical chlorination of ethylene glycol carbonate by means of chlorine or sulphuryl chloride.

This synthesis was published for the first time in 1953 by Newman und Addor (JACS, 1953, page 1263; JACS 1955, page 3789).

Ethylene glycol carbonate (GC) was photochlorinated as such by means of ultraviolet light at 60-70° C., and the resulting CGC was purified by vacuum distillation.

Newman and Addor obtained VC by elimination by means of triethylamine in boiling ether, the mixture having been heated overnight.

The isolation was effected by filtering off the triethylammonium chloride and then carrying out distillation, which gave a crude VC in a yield of 59%, which crude VC had to be purified by further distillation.

JP 2000/026449 describes the elimination in high-boiling solvents (b.p. 170-300° C.). The reaction is explicitly effected with triethylamine in dibutyl carbonate for 20 hours at 50° C. After the ammonium chloride has been filtered off and excess triethylamine distilled off, crude VC is isolated by simple distillation. In order to remove traces of amines, the VC is poured over a silica gel column. Finally, purifying distillation is carried out. The chlorine content of the VC thus obtained is stated at 29 ppm, whereas comparative samples contain >3000 ppm. The yield was 56%.

DE-A 19 955 944 claims the elimination in GC as a solvent (b.p. 243-244° C.). CGC is initially introduced in GC and reacted in 1.5 hours by addition of triethylamine at 60° C. After excess triethylamine has been distilled off at 40° C. and evaporation has been effected via a thin-film evaporator at 100° C., a colourless mixture of VC and GC is obtained in a yield of 73%. No data are given concerning the purity.

After the salts have been filtered off and the solvent and other impurities have been separated by simple distillation, the reactions of CGC in the liquid phase give a crude vinylene carbonate which is contaminated with residues of chloroacetaldehyde, chloroglycol carbonate, dichloroglycol carbonate and further organic compounds, some of which contain chlorine.

Johnson and Patton describe, in JOC, 1960, page 1042, the reaction of CGC over fixed beds of $CaSO_4$ catalysts in the gas phase at 250° C. and 50-60 mmHg.

The catalysts undergo very rapid deactivation and at best achieve a conversion of 35-40% at a selectivity of 40-45%. Higher or lower temperatures lead to a lower conversion. The catalysts can be regenerated by burning off.

Granulated active carbon and granulated activated alumina give only gaseous products.

DE-A 1 135 452 describes the HCl elimination of CGC at 300-400° C. The CGC is passed in gaseous form over an inert support material which is coated with elements of subgroup I, II or VIII of the Periodic Table of the Elements or salts or oxides thereof. Preferably, the chlorides of iron, of cobalt, of copper, particularly preferably cadmium chloride, are used. Suitable support materials are pumices and silicates having particle sizes of 4 to 8 mm.

The catalysts are operated as a stationary bed at atmospheric pressure or reduced pressure and a temperature of 270 to 450° C., preferably of 300-400° C.

The behaviour of $CdCl_2$ on pumice is explicitly described. The catalyst has a substantially longer on-stream time (about 270 hours) and higher selectivity (74%) than the $CaSO_4$ catalysts.

The space velocity was 0.15 kg of CGC per l of catalyst per hour and the inert gas stream was between 27 and 67 l per kg of CGC. The average conversion was 87%.

The catalyst can be burnt off at 500 to 700° C. with air.

The gas-phase process for the production of vinylene carbonate gives, after a simple distillation, a crude vinylene carbonate which is very similar to the liquid processes with regard to impurities.

Regarding the effort for purification by distillation, the data in the literature are inexact, so that it is not possible to estimate the effort expended in the specific case and the losses of yield due to the purification.

A high purity of the VC is of great technical importance particularly for the applications of polymerization and as an additive for battery electrolytes.

U.S. Pat. No. 2,873,230 states that, even with an 80-tray column, VC produced by the method of Newman and Addor cannot be sufficiently purified in order to be copolymerized with vinyl acetate, and insufficient molecular weights are achieved in the homopolymerization.

Chlorine-containing impurities are said to be responsible for this. The application relates to a purification method which consists in vaporizing the VC subjected to a purifying distillation and feeding it in gaseous form to thermal treatment at 200 to 450° C. The VC thus obtained is again subjected to purifying distillation, and only thereafter is a purity for satisfactory polymerization results achieved.

Huang et. al., in Chin. J. Polm. Sci. (1990) 8 (3), 197-203, state that VC produced by the method of Newman and Addor, after it has been isolated by filtration and the solvent distilled off, is stirred for 1 hour with about 4% of $NaBH_4$ at 64° C. and only thereafter subjected to a purifying distillation. This procedure must be repeated in order to obtain readily polymerizable material which is stable to discolouration.

Neither of the two literature references discusses in detail the content of impurities which has remained in the pure VC. Losses due to the isolation procedure are likewise not discussed.

It is an object of the invention to provide a process for the distillative purification of vinylene carbonate.

Surprisingly, it was found that the desired distillative properties of VC are achieved if, before the purifying distillation, a simple thermal treatment with organic compounds which have amidic nitrogen-hydrogen bonds is carried out. This is possible regardless of whether the industrial VC was obtained by elimination in the liquid phase or in the gas phase.

The invention relates to a process for the purification of vinylene carbonate, in which the vinylene carbonate to be purified a) is brought into contact at a temperature in the range of 25 to 180° C. with an organic compound having at least one amidic nitrogen-hydrogen bond, optionally with addition of solvent, b) any precipitated solid is optionally filtered off, c) and the purified vinylene carbonate is obtained from the remaining solution via a column distillation.

In the context of the invention, organic compounds having amidic nitrogen-hydrogen bonds are all aliphatic and aromatic carboxamides which have one or more of the following functional groups of the following formula (I)

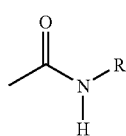

(I)

in which R=H, $C_1$-$C_{10}$-alkyl or cycloalkyl, $C_6$-$C_{10}$-aryl, or ureas of the following formula (II)

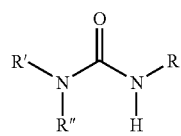

(II)

in which R, R' and R" are identical or different and are H, $C_1$-$C_{10}$-alkyl or cycloalkyl, $C_6$-$C_{10}$-aryl, ureas preferably being used.

Organic compounds having amidic nitrogen-hydrogen bonds from the group consisting of formamide, methylformamide, acetamide, methylacetamide, ethylacetamide, phenylacetamide, adipamide, benzamide, phthalamide, propionamide, dimethylurea, diethylurea, diphenylurea and urea are preferably used. Dimethylurea, diethylurea and diphenylurea are particularly preferably used. Urea is very particularly preferred.

The thermal treatment in step a) is effected with stirring at temperatures between 25 and 180° C., preferably between 60 and 160° C., particularly preferably between 90 and 140° C.

Relative to the vinylene carbonate, 0.1-30% by weight, preferably 1-10% by weight, particularly preferably 2-6% by weight, of the organic substance are added.

The addition of the organic compound having at least one amidic nitrogen bond can be effected in the presence of or without addition of solvents. For example, dimethylacetamide, N-methylpyrrolidone (NMP), dimethylformamide and DMOS may be mentioned as solvents.

After the thermal treatment, any precipitated solid is optionally filtered off and the vinylene carbonate is distilled off from the residue in step c). This can be carried out as a batch distillation from a container via a column having at least 10, preferably at least 20, particularly preferably at least 30, trays.

Suitable column internals are all possibilities known to the person skilled in the art, for example bubble trays, sieve trays and furthermore random packing, such as, for example, Raschig rings, Pall rings, Berl saddles, and also cross-channel structures, such as, for example the structured packings from Sulzer and Montz.

Below, the process according to the invention is illustrated with reference to some examples, but the examples are not to be understood as limiting the concept of the invention.

EXAMPLES

The distillation apparatus consisted of an oil-heated 15 l pot having a plane-ground joint and an anchor stirrer, column, reflux splitter, condenser and an apparatus for establishing a constant vacuum. A cold trap cooled to −78° C. was present before the vacuum pump. The pot having a plane-ground joint, column, reflux splitter and condenser were made of glass, and the anchor stirrer of Teflon.

The column had 1500 mm long Sulzer DX structured packing comprising Hastelloy C having a diameter of 50 mm. Structured packings of this type have separation efficiencies of between 15 and 30 trays per metre.

The apparatus was always blanketed with nitrogen before and after loading and before operation.

Crude VC freed substantially only from polymeric impurities by a preliminary distillation without a column was used as starting material.

This crude VC was about 97% pure and had a content of organic and inorganic chlorine of about 0.5% to 1%.

The gas chromatographic analysis was effected by means of an HP 6890. Separation was effected over a 50 metre long CP-Sil 8 CB having an ID of 0.53 mm and an FD of 1.0 μm.

The carrier gas was nitrogen at an admission pressure of 5 psi. The injector was operated with a flow of 138 ml/min and a split of 30/1.1 μl of pure VC was injected.

The injector temperature was 220° C., and the detector temperature 320° C. The temperature programme started with 50° C. with heating at 5° C./min to 250° C.

Evaluation was effected according to the standard % method.

Example 1

Comparative Example 7380 g of this crude VC was first heated with complete reflux in the apparatus described above at 34-35 mbar and first runnings were then distilled off at an R/E of 50. At a top temperature of 62 to 64° C., fractions having a total weight of about 1460 g, a VC content of 88 to 98% and a chlorine content above 5000 ppm distilled in about 40 hours. The bottom temperature increased from 66 to 70° C. during this procedure.

At a top temperature of 65 to 67° C. and a reflux ratio of 5/1, fractions having a total weight of about 3700 g, a VC content of about 99.5% and a chlorine content of about 1000 ppm then distilled within 21 hours.

The bottom temperature increased from 70 to 71° C. during this procedure and to 76° C. at the end.

220 g of VC having a content of about 99.2%, which had chlorine contents of >2000 ppm, then distilled over in 10 hours.

The bottom temperature increased from 77 to 84° C.

At the end, about 100 g of bottom product having a VC content of about 20% remained.

About 400 g of VC having a content of 37% was present in the cold trap.

The mass balance was 92% and the VC balance about 78%.

64% of the condensed material had been obtained as 99.5% pure VC.

Example 2

Example According to the Invention 200 g of urea were added to 12 060 g of crude VC and the mixture was stirred under nitrogen for 2 hours at 140° C. After cooling to about 30-40° C., 235 g of the solid were filtered off, 11 743 g of liquid were transferred to the distillation apparatus described above and 1000 g of NMP were added.

The mixture was refluxed at a pressure of about 35 mbar and then first runnings were distilled off at a reflux ratio of 30/1.

About 160 g of distillate which, according to GC analysis, comprised 96% of VC were thus obtained in the course of 2.5 hours. In the following 3.5 hours, about 400 g of a distillate which comprised 97.5% of VC were obtained, followed by about 470 g of distillate having a VC content of 99.4%, which distilled over in 2.5 hours.

The main run was then taken off at a reflux ratio of 5/1. About 9600 g of a 99.9% pure VC which had a chlorine content below 50 ppm distilled over in 26 hours.

About 1100 g of bottom product having a VC content of less than 0.5% remained.

The cold trap was virtually empty.

The mass balance was virtually quantitative, 93% of VC was recovered.

84% of the vinylene carbonate were obtained in the main fraction.

The invention claimed is:

1. Process for the purification of vinylene carbonate, comprising
    a) contacting vinylene carbonate to be purified at a temperature in the range of 25 to 180° C. with an organic compound having at least one amidic nitrogen-hydrogen bond,
    b) filtering off, in an optional step, any precipitated solid formed in step a) and
    c) distilling the remaining solution via a column distillation, optionally, in the presence of a solvent, to obtain purified vinylene carbonate.

2. Process according to claim 1, characterized in that organic compounds having amidic nitrogen-hydrogen bonds are aliphatic or aromatic carboxamides which have one or more functional groups of the formula (I)

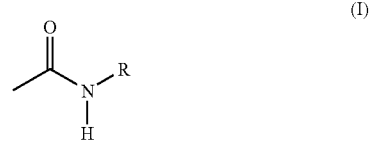

in which R=H, $C_1$-$C_{10}$-alkyl or cycloalkyl,
or ureas of the following formula (II)

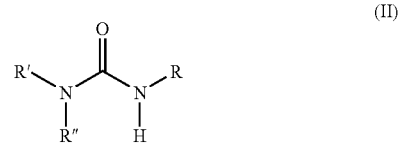

in which R, R' and R" are identical or different and are H, $C_1$-$C_{10}$-alkyl or cycloalkyl, $C_6$-$C_{10}$-aryl.

3. Process according to claim 2, characterized in that the compound of formula (I) or (II) is added in an amount of 0.1 to 30% by weight, based on vinylene carbonate, to the vinylene carbonate.

4. Process according to claim 1, characterized in that solvent used in the distillation step is dimethylacetamide, N-methylpyrrolidone, dimethylformamide or DMSO.

* * * * *